United States Patent
Chhabra et al.

(10) Patent No.: US 11,335,442 B2
(45) Date of Patent: May 17, 2022

(54) GENERATION OF CONCEPT SCORES BASED ON ANALYSIS OF CLINICAL DATA

(71) Applicant: International Business Machines Corporation, Armonk, NY (US)

(72) Inventors: Swapnil Chhabra, Arlington Heights, IL (US); Piyush Madan, Boston, MA (US); Jeffrey B Beers, Issaquah, WA (US); Joern Jaskolowski, Copenhagen (DK); Terry Verne Taerum, Aurora, IL (US)

(73) Assignee: International Business Machines Corporation, Armonk, NY (US)

( * ) Notice: Subject to any disclaimer, the term of this patent is extended or adjusted under 35 U.S.C. 154(b) by 433 days.

(21) Appl. No.: 16/100,536

(22) Filed: Aug. 10, 2018

(65) Prior Publication Data

US 2020/0051673 A1 Feb. 13, 2020

(51) Int. Cl.
*G16H 10/60* (2018.01)
*G16H 10/40* (2018.01)
*G06F 16/2457* (2019.01)

(52) U.S. Cl.
CPC ....... *G16H 10/60* (2018.01); *G06F 16/24578* (2019.01); *G16H 10/40* (2018.01)

(58) Field of Classification Search
CPC ........ G06Q 50/22; G06Q 50/24; G16H 10/60; G16H 50/30; G16H 15/00; G16H 50/20;
(Continued)

(56) References Cited

U.S. PATENT DOCUMENTS 6,193,654 B1  2/2001  Richardson et al.
9,754,220 B1  9/2017  Brestoff et al.
(Continued)

FOREIGN PATENT DOCUMENTS

WO    2014182725 A1    11/2014

OTHER PUBLICATIONS

Distributed analyses of disease risk and association across networks of de-identified medical systems McMurry, Andrew J . . . ProQuest Dissertations and Theses ProQuest Dissertations Publishing. (2015) (Year: 2015).*

(Continued)

*Primary Examiner* — Joseph D Burgess
(74) *Attorney, Agent, or Firm* — Patterson + Sheridan, LLP

(57) ABSTRACT

Techniques for clinical concept score generation are provided. A set of keywords related to a clinical concept are determined, and a plurality of attributes is identified by searching a plurality of electronic health records (EHRs) based on the set of keywords. A plurality of attribute groups is generated, where each of the attribute groups is statistically orthogonal and includes at least one of the plurality of attributes, based on occurrence data extracted from the plurality of EHRs. For a patient, a plurality of attribute scores is determined for the plurality of attributes based on occurrence data extracted from one or more EHRs corresponding to the patient. A plurality of attribute group scores is determined, for the patient, for the plurality of attribute groups, based on the plurality of attribute scores. A clinical concept score is generated for the patient based on the plurality of attribute group scores.

20 Claims, 9 Drawing Sheets

(58) Field of Classification Search
CPC ...... G16H 50/70; G16H 50/50; A61B 5/7275; A61B 5/7264
See application file for complete search history.

(56) References Cited

U.S. PATENT DOCUMENTS

| | | | | |
|---|---|---|---|---|
| 2002/0040183 | A1* | 4/2002 | Iliff | G16H 10/60 600/300 |
| 2005/0261941 | A1* | 11/2005 | Scarlat | G16H 50/70 705/3 |
| 2007/0026365 | A1* | 2/2007 | Friedrich | G16B 5/00 434/127 |
| 2008/0059391 | A1* | 3/2008 | Rosales | G16H 50/20 706/12 |
| 2008/0195420 | A1 | 8/2008 | Ramelson et al. | |
| 2008/0201280 | A1* | 8/2008 | Martin | G06Q 50/24 706/12 |
| 2011/0129129 | A1* | 6/2011 | Avinash | G16H 50/20 382/128 |
| 2014/0372146 | A1 | 12/2014 | Kramer | |
| 2015/0006199 | A1* | 1/2015 | Snider | G16H 50/20 705/3 |
| 2015/0310177 | A1* | 10/2015 | Csurka | G06N 5/02 706/50 |
| 2015/0347705 | A1 | 12/2015 | Simon et al. | |
| 2016/0120481 | A1 | 5/2016 | Li et al. | |
| 2017/0132373 | A1 | 5/2017 | King et al. | |
| 2017/0270257 | A1 | 9/2017 | St. Clair et al. | |

OTHER PUBLICATIONS

Chan LW, Liu Y, Chan T, et al. PubMed-supported clinical term weighting approach for improving inter-patient similarity measure in diagnosis prediction. BMC Med Inform Decis Mak. 2015;15:43. Published Jun. 2, 2015. doi:10.1186/s12911-015-0166-2 (Year: 2015).*
Charleson et al. "Validation of a combine comorbidity index," Journal of Clincial Epidemiology, Nov. 1994 </issue/S0895-4356(00)X0188-6>vol. 47, Issue 11, pp. 1245-1251.
Quan, "Updating and Validating the Charlson Comorbidity Index and Score for Risk Adjustment in Hospital Discharge Abstracts Using Data From 6 Countries," American Journal of Epidemiology, vol. 173, No. 6, DOI: 10.1093/aje/kwq433, Feb. 17, 2011, 7 pages.
Deyo, et al., "Adapting A Clinical Comorbidity Index For Use With ICD-9-CM Administrative Databases," J Clin Epidemiol, vol. 45, No. 6, pp. 613-619, 1992, 7 pages.
Elixhauser, et al. "Comorbidity Measures for Use with Administrative Data," Medical Care, vol. 36, No. 1, pp. 6-27, 1999.
Chronic Condition Indicator (CCI) for ICD-9-CM, HCUP-US Tools & Software Page [Accessed Online Aug. 9, 2018] <https://www.hcup-us.ahrq.gov/toolssoftware/chronic/chronic.jsp>.
McGregor et al., "Utility of the Chronic Disease Score and Charlson Comorbidity Index as Comorbidity Measures for Use in Epidemiologic Studies of Antibiotic-resistant Organisms," American Journal of Epidemiology, Mar. 1, 2005, 31 pages.
Glasheen et. al, "Diabetes Complications Severity Index (DCSI)-Update and ICD-10 translation," J Diabetes Complications, Jun. 2017; 31(6): 1007-1013, 2 pages.
Wilson et al., Prediction of Coronary Heart Disease Using Risk Factor Categories, Downloaded from http://ahajournals.org by on Aug. 9, 2018.
Mark T. Keegan, Ognjen Gajic, and Bekele Afessa, "Severity of illness scoring systems in the intensive care unit," Critical Care Medicine, vol. 39, No. 1, pp. 163-169, 2011.
University of Manitoba, "Concept: Charlson Comorbidity Index," Last Updated: Jan. 22, 2016, 10 pages.

* cited by examiner

GENERATION OF CONCEPT SCORES BASED ON ANALYSIS OF CLINICAL DATA

BACKGROUND

The present disclosure relates to clinical concept scoring, and more specifically, to generating objective scores for clinical concepts based on comprehensive analysis of electronic health records.

In determining appropriate treatments for particular patients, it is often important to understand not only the affliction that the patient suffers from, but also the severity of the illness. Summarizing a patient's medical condition, however, is highly subjective and does not consider a wide variety of relevant data. Instead, healthcare professionals rely on their subjective experiences and observations. Further, based on existing scales, it is impossible to effectively compare patients with the same affliction due to the subjective nature of each determination, the relative paucity of data that is considered, and the simple fact that many conditions are not fully understood, which prevents a complete and comprehensive understanding of each factor or attribute involved.

SUMMARY

According to one embodiment of the present disclosure, a method is provided. The method includes determining a set of keywords related to a clinical concept, and identifying a plurality of attributes by searching a plurality of electronic health records (EHRs) based on the set of keywords. The method further includes generating a plurality of attribute groups by operation of one or more computer processors, wherein each of the attribute groups is statistically orthogonal and includes at least one of the plurality of attributes, based on occurrence data extracted from the plurality of EHRs. Additionally, the method includes determining, for a first patient, a plurality of attribute scores for the plurality of attributes based on occurrence data extracted from one or more EHRs corresponding to the first patient. The method also includes determining, for the first patient, a plurality of attribute group scores for the plurality of attribute groups, based on the plurality of attribute scores. Finally, a clinical concept score is generated for the first patient, based on the plurality of attribute group scores.

According to a second embodiment of the present disclosure, a computer program product is provided. The computer program product includes a computer-readable storage medium having computer-readable program code embodied therewith, the computer-readable program code executable by one or more computer processors to perform an operation. The operation includes determining a set of keywords related to a clinical concept, and identifying a plurality of attributes by searching a plurality of EHRs based on the set of keywords. The operation further includes generating a plurality of attribute groups, wherein each of the attribute groups is statistically orthogonal and includes at least one of the plurality of attributes, based on occurrence data extracted from the plurality of EHRs. Additionally, the operation includes determining, for a first patient, a plurality of attribute scores for the plurality of attributes based on occurrence data extracted from one or more EHRs corresponding to the first patient. The operation also includes determining, for the first patient, a plurality of attribute group scores for the plurality of attribute groups, based on the plurality of attribute scores. Finally, a clinical concept score is generated for the first patient, based on the plurality of attribute group scores.

According to a third embodiment of the present disclosure, a system is provided. The system includes one or more computer processors, and a memory containing a program which when executed by the one or more computer processors performs an operation. The operation includes determining a set of keywords related to a clinical concept, and identifying a plurality of attributes by searching a plurality of EHRs based on the set of keywords. The operation further includes generating a plurality of attribute groups, wherein each of the attribute groups is statistically orthogonal and includes at least one of the plurality of attributes, based on occurrence data extracted from the plurality of EHRs. Additionally, the operation includes determining, for a first patient, a plurality of attribute scores for the plurality of attributes based on occurrence data extracted from one or more EHRs corresponding to the first patient. The operation also includes determining, for the first patient, a plurality of attribute group scores for the plurality of attribute groups, based on the plurality of attribute scores. Finally, a clinical concept score is generated for the first patient, based on the plurality of attribute group scores.

DETAILED DESCRIPTION

Embodiments of the present disclosure provide a solution for the problem of summarizing patient medical conditions for symptomatology or utilization concepts using available electronic health record (EHR) data, where conventional scoring approaches are not available or cannot be applied. In embodiments, a patient's medical condition can be summarized by developing a range of clinical scores from the patient's EHRs, which allows for objective determination as to the severity of conditions, as well as direct comparison to other patients. In an embodiment, an initial cognitive approach suggests keywords best suited to identify key attributes of the EHRs related to the clinical theme. In one embodiment, one or more machine learning models are utilized to generate these keywords. In another embodiment, one or more keywords are manually defined or specified. Attributes can include diagnoses, observations, drugs, procedures, encounters, findings, and various other types. In one embodiment, these attributes are then categorized into orthogonal groups of core clinical concepts using factor analysis, and if necessary, in some embodiments, are further clinically classified.

In an embodiment, attributes can be compared to population norms and individual scores can be combined to provide an estimate of clinical impact for the overall concept. In some embodiments, concepts can be any identified and optionally named grouping that relates attributes for clinical characteristics (e.g., presence of symptoms, complications, comorbidities, etc.) or for utilization (e.g., visit type and frequency, medication use, etc.). In an embodiment, each attribute group is clinically distinct, and concept scores for groups of clinically related attributes can serve as proxies for impact due to that concept where more conventional scoring methods are not available. Scoring of attributes within concepts can use a variety of techniques, including binary techniques, and can also be normalized with limits set by analyzing the range of values observed in the cohort. In some embodiments, individual attribute group scores are weighted, and aggregated into a single clinical impact score for the entire clinical theme. Thus, embodiments of the present disclosure provide a rigorous way of scoring a patient's medical state. Embodiments of the present disclosure are therefore a significant improvement over the experience-based assessment made by healthcare providers based on a patient's medical chart.

Figure 1:
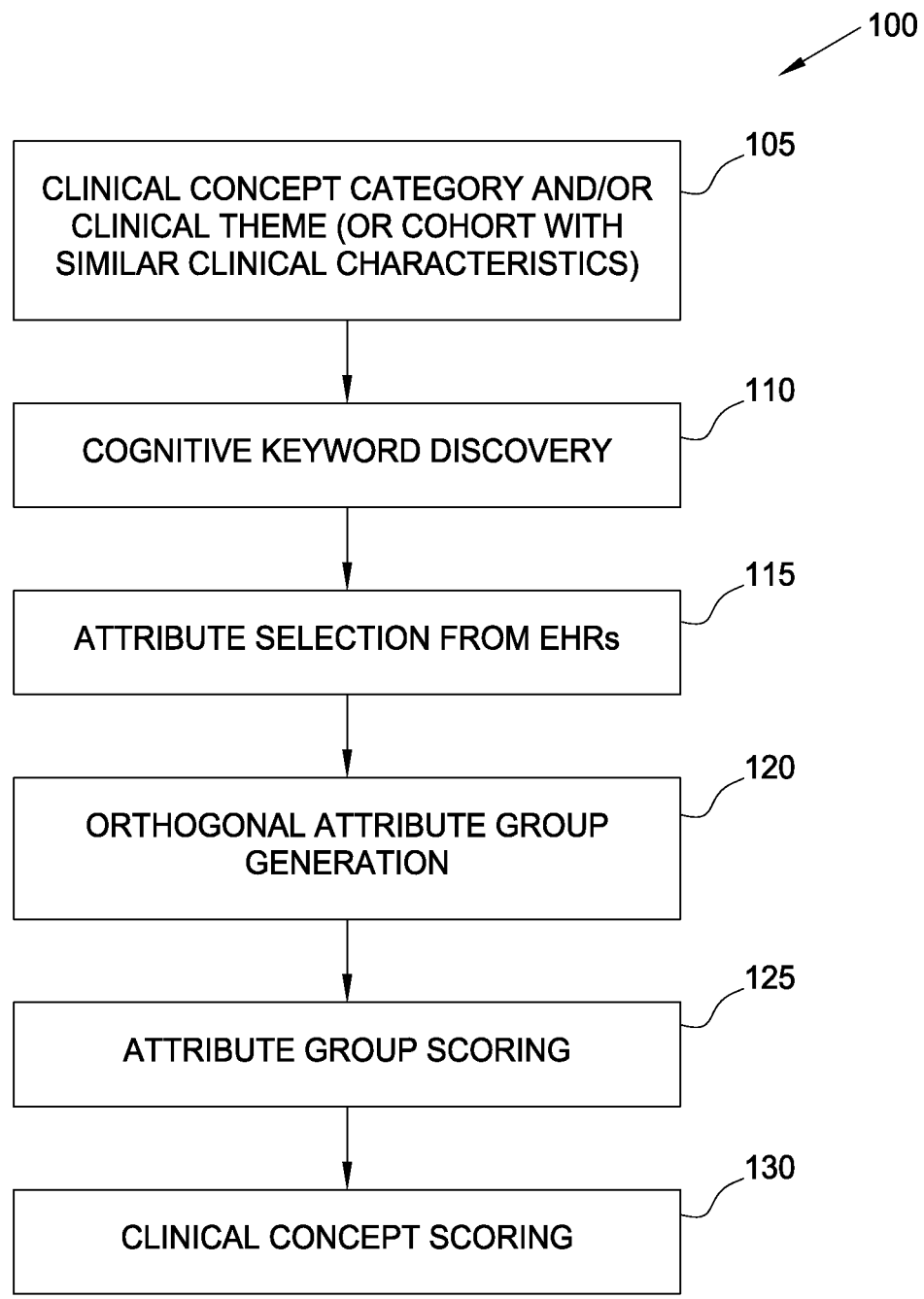
FIG. 1 is a flow diagram illustrating a workflow for generating clinical concept scores, according to one embodiment disclosed herein.

FIG. 1 is a flow diagram illustrating a workflow 100 for generating clinical concept scores, according to one embodiment disclosed herein. In the illustrated embodiment, the workflow 100 begins at block 105, with the identification of a clinical concept category and/or clinical theme. In an embodiment, the clinical concept/theme refers to the concept that the user wishes to study and score, such as "schizophrenia" or "diabetes." In some embodiments, the concept or theme can also include additional detail, such as "psychosocial indices" in conjunction with diagnosed schizophrenia. Once the desired clinical concept is identified, at block 110, keywords are identified. In some embodiments, the keywords are predefined in association with the concept. In other embodiments, one or more cognitive tools or methods are used to analyze the concept(s) and generate or identify keywords based on medical literature, as will be discussed below in more detail.

Once one or more keywords related to the concept have been identified, the workflow 100 continues to block 115, where attributes are identified and selected from EHR data. In one embodiment, block 115 corresponds to a keyword search of the EHRs based on the generated keywords. In one embodiment, attribute selection involves utilizing one or more natural language processing (NLP) models to parse the EHR data. In an embodiment, the EHRs that are processed to select attributes includes data corresponding to any number of patients, rather than solely the patient which is under consideration. In one embodiment, all of the available EHRs are analyzed. In some embodiments, only EHRs corresponding to a specified cohort of patients (such as patients that are in some way similar to the index patient) are considered. In some embodiments, EHRs corresponding to patients who are associated with the selected concept are considered when selecting attributes. For example, in one embodiment, if the concept under inspection is "schizophrenia," the EHRs parsed in block 115 may correspond to patients who have been diagnosed with schizophrenia. In some embodiments, the index patient (i.e., the patient that is being considered, and for whom the concept score is being generated) may or may not be included within the EHRs that are analyzed in block 115.

In one embodiment, the attributes correspond to items such as diagnoses, findings, lab results, observations, procedures, drug use, genes, single nucleotide polymorphisms (SNP), encounters, and the like. For example, if an identified keyword is "depression," the attribute search may include searching the EHRs based on the keyword "depression" to identify occurrences of relevant diagnoses (attributes), such as "depressive disorder," "major depression," "recurrent depression," and the like. In one embodiment, the attributes include data such as SNOMED IDs, CPT codes, ICD9/10 codes, and the like. Generally, attributes may include any data about a patient that describe a patient or have some bearing on a patient's symptoms, condition, treatment, or progression.

At block 120, the selected attributes are processed to identify groups of related attributes. In some embodiments, factor analysis or principal component analysis is performed on the selected attributes (e.g., on occurrence data corresponding to the attributes) to generate orthogonal groups. That is, in an embodiment, the attributes are processed to identify orthogonal groups of related attributes, such that each group has an independent effect on the patient's condition, without interaction (or with minimal interaction) between each group. In some embodiments, each attribute is assigned to a group without consideration as to the keyword that was used to select the attribute. Thus, in some embodiments, a single keyword can produce attributes that may belong to differing groups. In other embodiments, all attributes corresponding to a particular keyword are assigned to the same group, and orthogonal group generation essentially comprises clustering the keywords into groups.

Once the groups have been determined, the workflow 100 proceeds to block 125, where each group is scored for the index patient. This attribute scoring process may include a variety of techniques discussed in more detail below. In some embodiments, the score for each attribute group is based on the score for each individual attribute within the respective group. Finally, at block 130, an overall clinical concept score is generated for the index patient. In some embodiments, the concept score is similarly based on the individual group scores for the patient. In this way, an objective and comprehensive value is determined which represents the patient's condition. This value can be compared to other patients with similar conditions, other patients in the index patient's cohort, or all patients.

In some embodiments, clinical concept scores are generated for a particular patient at various times, so that the progression of the patient's condition can be compared over time. For example, in one embodiment, when scoring each attribute for the patient, EHRs of the patient corresponding to a defined time period may be used. In this way, the resulting concept score is based on the patient's condition during that time period. In some embodiments, a concept score is generated for a single patient for multiple time periods, such as the current condition (using data within a predefined period of time, such as the last six months or the last year), as well as a condition at various points in time (such as using EHR data from the previous year, the year before that, and so on). In this way, the progression of the clinical concept, with respect to the particular patient, can be objectively tracked and monitored over time.

Further, in addition to comparing the final concept score between patients or between different times, embodiments of the present disclosure enable comparison of the various sub-scores (e.g., the attribute scores and the group scores) among patients and at various points in time. For example, utilizing embodiments of the present disclosure, a particular attribute score for a particular patient during a particular window of time can be compared to any number of other scores for the same attribute, where the other scores may correspond to the same patient at a different time, a different patient at the same time, or a different patient at a different time. Similar comparisons are possible based on the attribute groups, which enables a user to compare each group score to other group scores at differing times or for differing patients.

Figure 2:
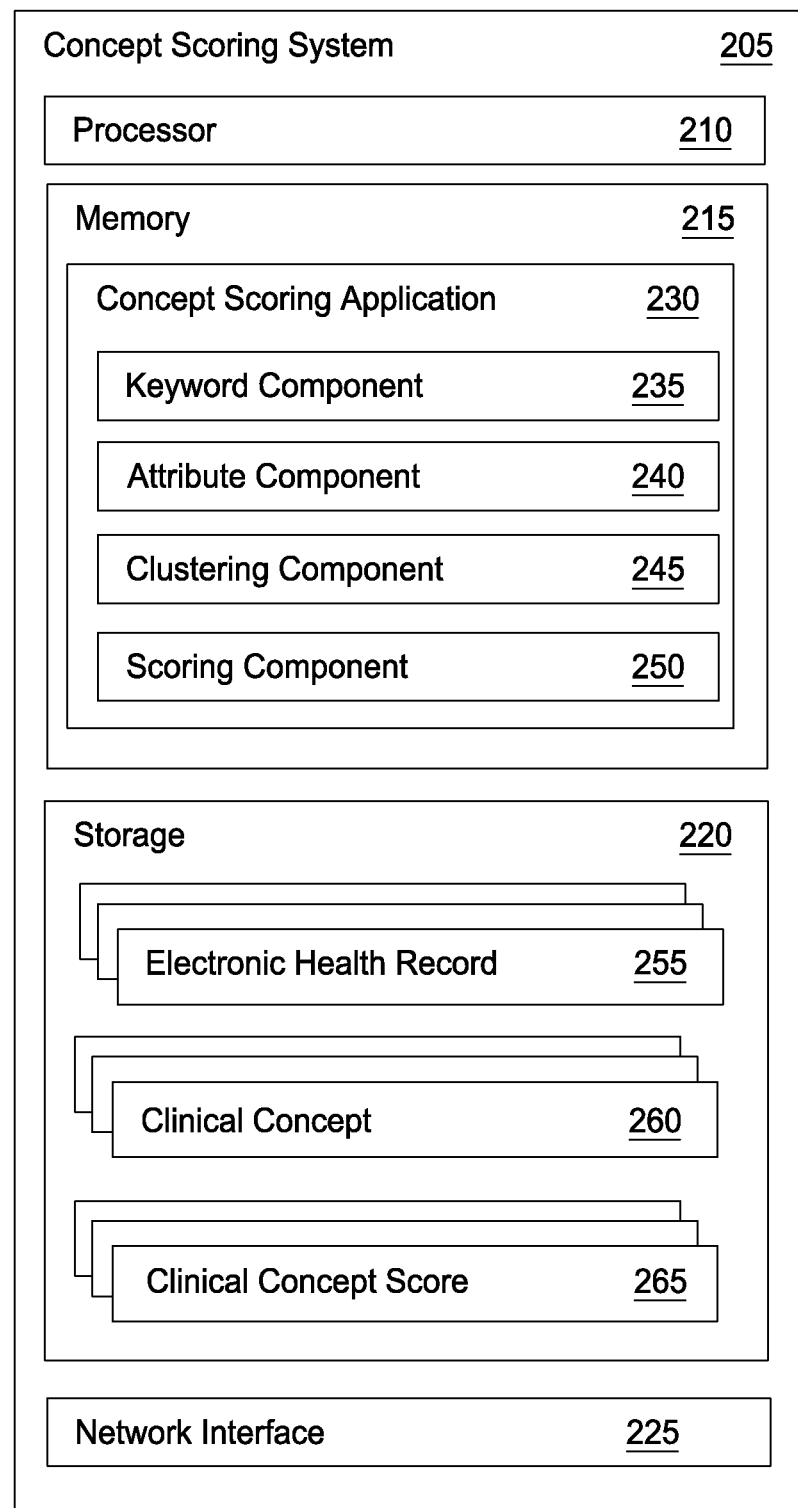
FIG. 2 is a block diagram of a concept scoring system, according to one embodiment disclosed herein.

FIG. 2 is a block diagram of a Concept Scoring System 205, according to one embodiment disclosed herein. As illustrated, the Concept Scoring System 205 includes a Processor 210, a Memory 215, Storage 220, and a Network Interface 225. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Through the Network Interface 225, the Concept Scoring System 205 may be communicatively coupled with other devices, including data stores containing EHRs, terminals or devices used by healthcare providers, and the like.

In the illustrated embodiment, the Storage 220 includes one or more EHRs 255, Clinical Concepts 260, and Clinical Concept Scores 265. Although illustrated as residing in Storage 220, in various embodiments, the EHRs 255 can reside in remote databases or data stores, or may be split across multiple data stores (including Storage 220). In an embodiment, the Clinical Concepts 260 include data structures for each concept that has been identified and processed. For example, in one embodiment, once the Concept Scoring Application 230 generates a concept score for a particular concept, information about the relevant keywords, attributes, and attribute groups is stored within the Clinical Concepts 260. In this way, if a user wishes to score another patient based on the same concept, the Concept Scoring Application 230 can access the stored Clinical Concept 260 in order to process only the particular patient's EHRs and avoid incurring duplicate processing requirements to identify the attribute groups.

In an embodiment, the Clinical Concept Scores 265 correspond to generated concept scores for one or more patients, and across one or more concepts as well as corresponding to one or more time periods. In one embodiment, the Concept Scoring Application 230 stores all generated concept scores for future reference and to facilitate comparisons between patients and across time periods. In the illustrated embodiment, the Memory 215 contains a Concept Scoring Application 230. Illustratively, the Concept Scoring Application 230 includes a Keyword Component 235, an Attribute Component 240, a Clustering Component 245, and a Scoring Component 250. Although discussed as discrete components for illustration, in embodiments, the operations of each component may be combined or divided into any number of components, depending on the particular implementation. Further, in various embodiments, each component may be implemented in software, hardware, or a combination of both software and hardware.

In an embodiment, the Keyword Component 235 receives an indicated concept (such as from a healthcare provider), and identifies or generates one or more keywords that are relevant to the concept. For example, in one embodiment, the Keyword Component 235 utilizes a cognitive method that parses medical literature based on the concept, to identify related concepts or keywords for the concept. In one embodiment, a tool such as Watson for Drug Discovery, created by IBM of Armonk, N.Y., is utilized to identify keywords for the provided concepts. In some embodiments, the Keyword Component 235 identifies keywords that have a predefined relationship or association with the concept. For example, in some embodiments, healthcare providers can define keywords for concepts, and when the concept is subsequently entered, this list of predefined keywords can be utilized in addition to or instead of cognitive keyword generation. Further, in some embodiments, any keywords identified are first validated or approved by a healthcare professional or the user prior to use, in order to ensure they are clinically relevant to the indicated concept.

In the illustrated embodiment, the Attribute Component 240 utilizes the keywords for the concept to parse EHRs 255 to identify attributes. In embodiments, this process may be based on one or more NLP models or searches through the EHRs 255 to select attributes that are relevant to each keyword. In one embodiment, in addition to identifying relevant attributes, the Attribute Component 240 maintains occurrence data for each attribute indicating how often the attribute is identified in the EHR data, the patient(s) associated with that data, and the like. Additionally, in some embodiments, one or more attributes can be selected or identified manually. Similarly, in one embodiment, the automatically generated attributes are clinically validated prior to clustering. In the illustrated embodiment, the Clustering Component 245 performs factor analysis (such as exploratory factor analysis), principal component analysis, or other similar operations in order to identify orthogonal groups of attributes. In an embodiment, the orthogonality of the groups minimizes bias when aggregating the attribute scores, and ensures accurate results.

In some embodiments, occurrence data with respect to each attribute from a plurality of patients is processed by the Clustering Component 245 to determine attributes that are related in order to generate the groups. In some embodiments, the Clustering Component 245 may ensure that all attributes related to a particular keyword are assigned to the same group. In other embodiments, attributes may be assigned to differing groups, even if they were retrieved using the same keyword.

In the illustrated embodiment, the Scoring Component 250 processes EHRs for each particular patient in order to generate attribute scores, group scores, and finally, a comprehensive concept score for the desired concept(s). These generated scores may then be utilized in various ways. For example, the attribute scores may be analyzed to determine which attribute(s) are most affecting the patient's final score. Similarly, the attribute group scores may be processed to determine which groups of attributes are most relevant or important. Further, the attribute scores, attribute group scores, and concept scores may be compared among patients or over time. In this way, embodiments of the present disclosure enable objective and comprehensive clinical concept analysis that can significantly improve medical care.

Figure 3:
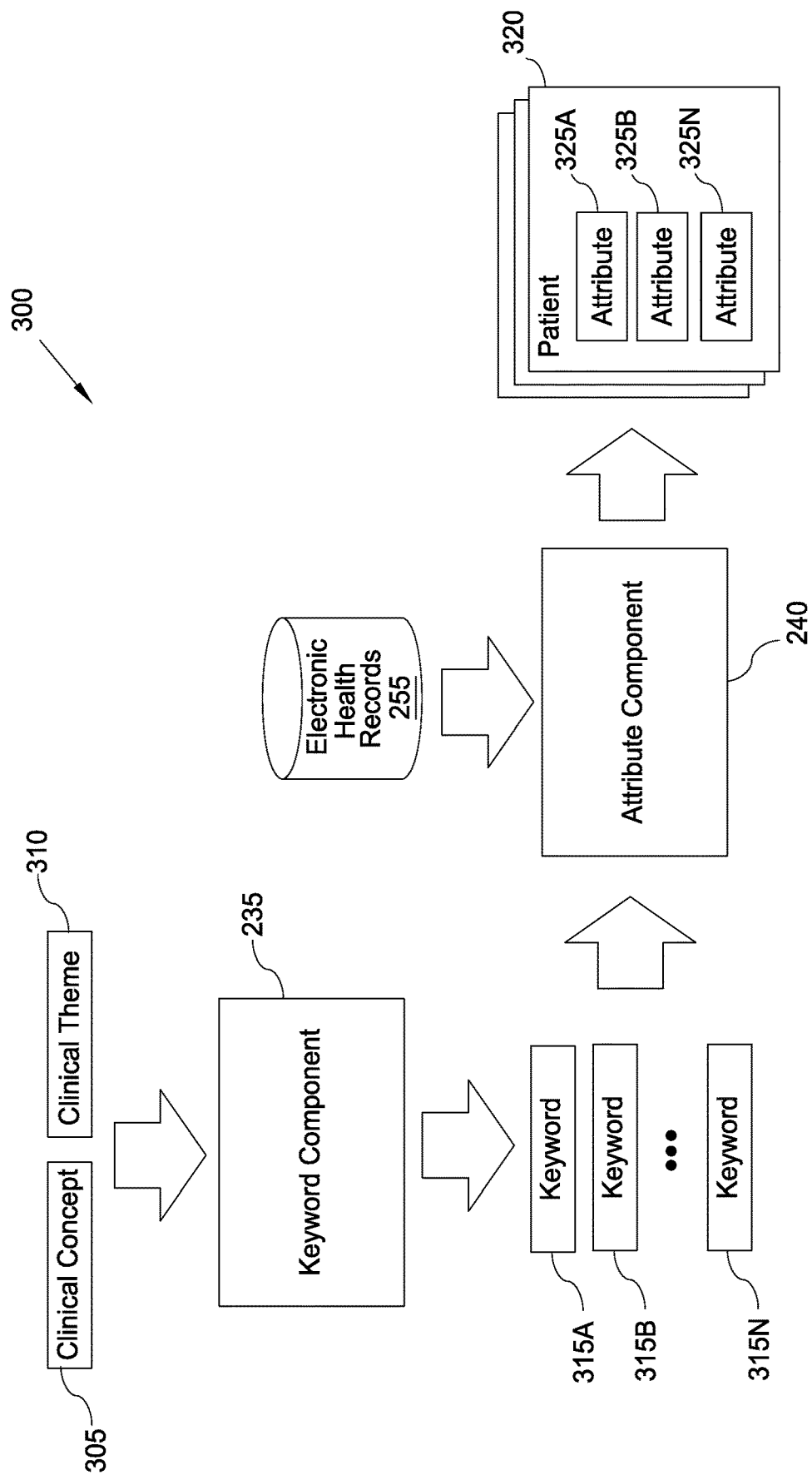
FIG. 3 is a block diagram illustrating a workflow for attribute selection, according to one embodiment disclosed herein.

FIG. 3 is a block diagram illustrating a workflow 300 for attribute selection, according to one embodiment disclosed herein. In the illustrated embodiment, one or more Clinical Concept(s) 305 and one or more Clinical Theme(s) 310 are provided to the Keyword Component 235. As discussed above, in some embodiments, a single concept or theme is utilized. In one embodiment, example clinical themes might include schizophrenia, diabetes, or rheumatoid arthritis, while example concepts might include psychosocial index, complications, or medication utilization. Of course, in embodiments, the concept may be defined as broadly or as narrowly as the user desires, and may include both a concept category and a theme. As illustrated, the Keyword Component 235 generates one or more Keywords 315A-N. For example, utilizing the input terms "schizophrenia" and "psychosocial index" with a cognitive search tool, medical literature was parsed to identify keywords, 18 of which were selected and clinically validated for use. For purposes of example and not limitation, these keywords included "abuse," "alcohol," "anxiety," "bipolar," "cannabis," "catatonia," "cognition," "dementia," "depression," "development," "hallucinations," "mania," "motor," "phobias," "schizophrenia," "social," "stress," and "victim."

In the illustrated workflow, the Attribute Component 240 receives the Keywords 315A-N, and uses them to search the EHRs 255 to identify and select attributes. In the illustrated embodiment, data corresponding to a plurality of Patients 320 is identified, including occurrence data for each of a plurality of Attributes 325A-N for each patient 320. In this way, the occurrence data can be processed using factor analysis and/or principal component analysis to identify groups of attributes.

Figure 4:
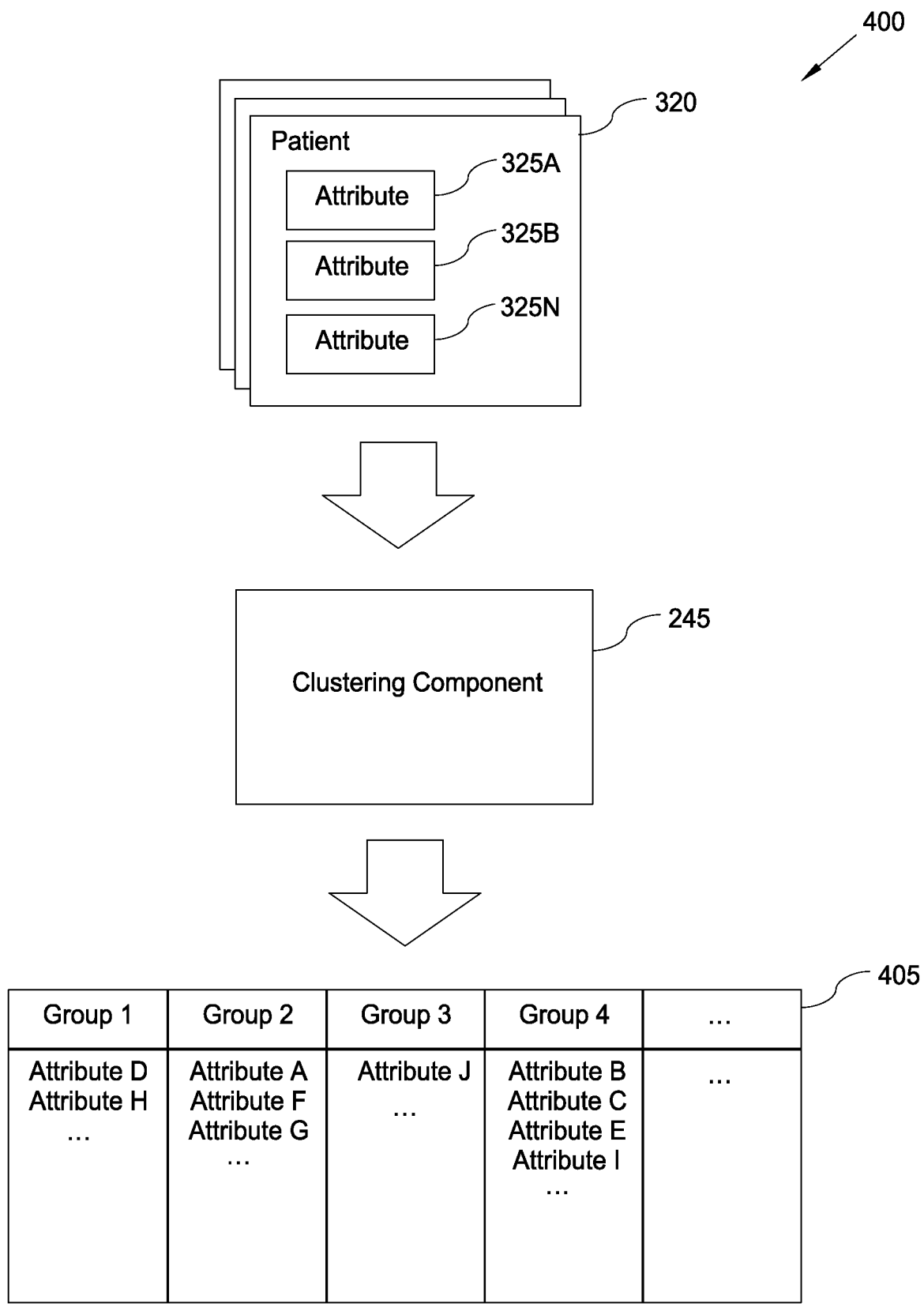
FIG. 4 is a block diagram illustrating a workflow for attribute group generation, according to one embodiment disclosed herein.

FIG. 4 is a block diagram illustrating a workflow 400 for attribute group generation, according to one embodiment disclosed herein. In the illustrated embodiment, the Attributes 325A-N are ingested and processed by the Clustering Component 245 to generate any number of Groups 405, each of which includes one or more Attributes 325A-N. In one embodiment, a user or administrator defines the number of groups to generate. In other embodiments, the Clustering Component 245 determines the number of groups required to ensure the generated groups are adequately orthogonal. Continuing the above example, the 18 identified keywords were used to search EHR data corresponding to 123,000 patients, and 308 attributes were identified. These attributes were processed using factor analysis to identify six distinct attribute groups or concept groups, illustrated below in Table 1. In Table 1, rather than list each distinct attribute, the 18 keywords are depicted in each respective group, along with an indication as to how many attributes were identified for each keyword.

TABLE 1

| Group 1 |
|---|
| Social (4 attributes) |
| Victim (8 attributes) |
| Group 2 |
| Catatonia (8 attributes) |
| Cognition (6 attributes) |
| Development (13 attributes) |
| Dementia (23 attributes) |
| Motor (10 attributes) |
| Group 3 |
| Anxiety (10 attributes) |
| Hallucinations (4 attributes) |

TABLE 1-continued

| Phobias (13 attributes) |
|---|
| Stress (9 attributes) |
| Group 4 |
| Abuse (14 attributes) |
| Group 5 |
| Bipolar (36 attributes) |
| Depression (34 attributes) |
| Mania (1 attribute) |
| Schizophrenia (45 attributes) |
| Group 6 |
| Alcohol (54 attributes) |
| Cannabis (15 attributes) |

Once these attributes are identified and grouped, in one embodiment, the Concept Scoring Application 230 stores these associations as Clinical Concepts 260 in the Storage 220 for later use. If a user subsequently wishes to generate a concept score for additional patients or additional timeframes, the stored Clinical Concept 260 may be utilized rather than regenerating keywords, reparsing the EHRs to select attributes, and reprocessing of the attributes to identify the groups. In some embodiments, these models may be periodically refined or regenerated in order to ensure they remain current. For example, the Concept Scoring Application 230 may periodically determine keywords again based on any updated literature, select attributes based on updated EHR data, and generate new attribute groups. As discussed below, for each particular patient, the concept score can be generated in various ways. In embodiments, generally, for each patient, each attribute is scored, and these scores are aggregated to generate the group scores for the patient. These group scores are then similarly aggregated to compute the final concept score.

In some embodiments, the attribute groups are named in order to facilitate understanding. In one embodiment, the generated groups are manually named (e.g., by a healthcare provider or subject matter expert) to describe the attributes included in the respective group. In some embodiments, a machine learning model is trained to name each group, based on applying NLP models to the attributes and/or keywords within each group. For example, for the groups specified in Table 1, Group 1 may be labeled "Patient Support." Although not illustrated, in embodiments, this group may also include keywords and attributes such as "family," "housing," and the like. Similarly, Group 2 may be labeled "Functional" because the included attributes describe how functional the patient is. Further, Group 3 may be labeled "Symptoms," Group 4 may be labeled "Harm," Group 5 may be labeled "Diagnosis," and Group 6 may be labeled "Substances." Of course, these labels are provided for illustration, and are not intended to be limiting on the embodiments disclosed herein.

Figure 5:
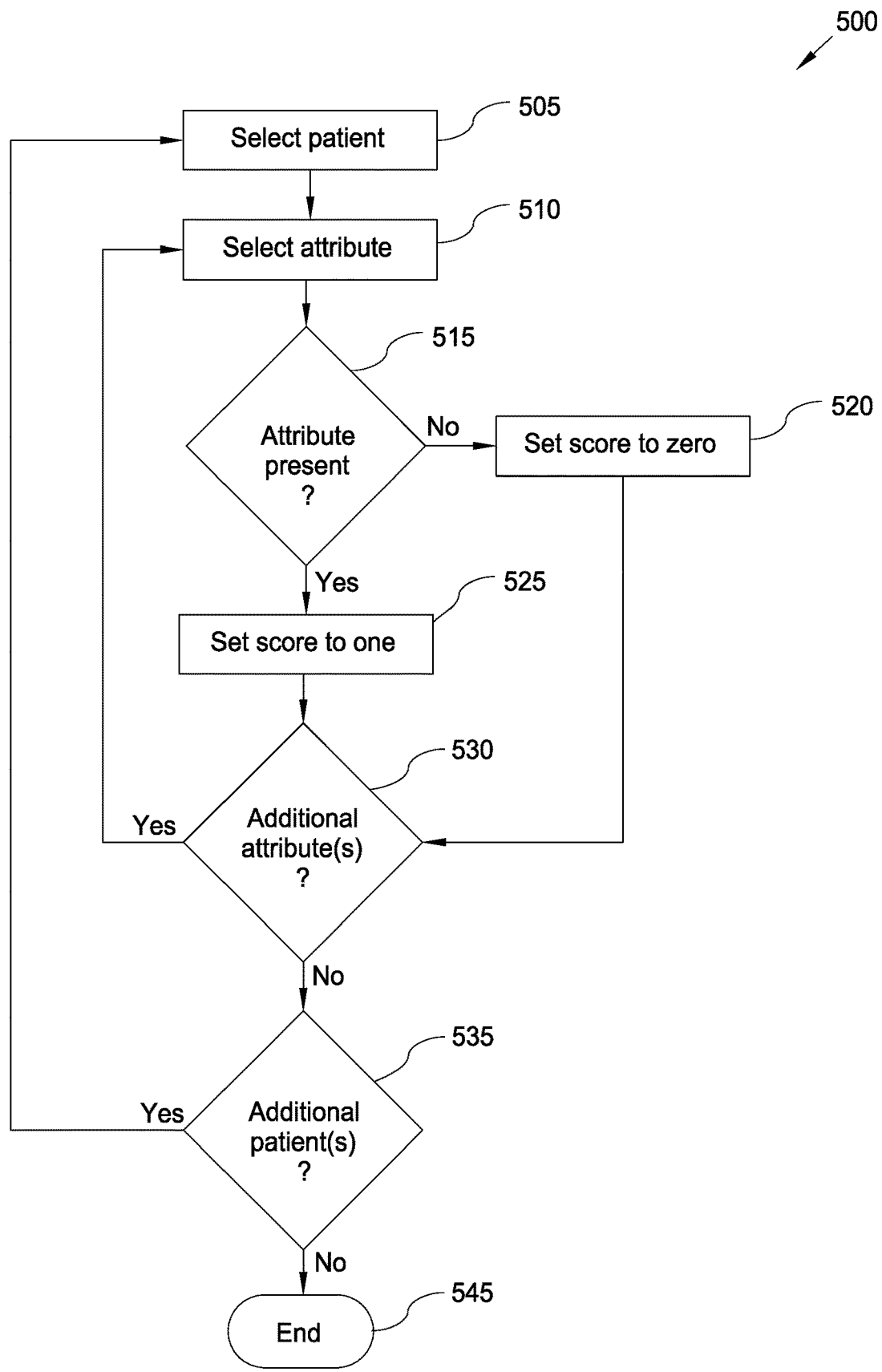
FIG. 5 is a flow diagram illustrating a method for attribute scoring, according to one embodiment disclosed herein.

FIG. 5 is a flow diagram illustrating a method 500 for attribute scoring, according to one embodiment disclosed herein. The method 500 corresponds to a binary scoring algorithm, which considers only whether or not each attribute is present in the patient's EHR data, and the attribute scores are not related to the magnitude of each attribute (e.g., how often or how frequently the attribute is found in the EHR data). The method 500 begins at block 505, where the Scoring Component 250 selects a patient. In some embodiments, selecting a patient comprises receiving a selected patient from a user (e.g., a healthcare provider) that selected the index patient he or she wishes to analyze.

The method 500 then proceeds to block 510, where the Scoring Component 250 selects an attribute from the Attributes 325A-N that where identified in the EHR data. At block 515, the Scoring Component 250 determines whether the selected attribute is present at least once in the EHR data corresponding to the selected patient. For example, if the selected attribute is "major depression, single episode," the Scoring Component 250 determines whether this attribute (or the concept ID corresponding to this attribute) is found at least once in the various files and data associated with the selected patient. In some embodiments, the Scoring Component 250 considers all of the patient's available EHR data. In some embodiments, the Scoring Component 250 considers only a subset of the patient's EHR data, such as EHR data corresponding to a defined time period. In some embodiments, the user may select the relevant time period, in order to generate scores representing the patient's condition during the selected time period. In some embodiments, the user may select multiple time periods, and the Scoring Component 250 may generate separate scores for each time period.

If the Scoring Component 250 determines that the attribute is present at least once in the selected data, the method 500 continues to block 525, where the Scoring Component 250 sets the attribute score of the selected attribute to one. Although "1" is used for illustrative purposes, in embodiments, any value may be utilized to signify the presence of the attribute. The method 500 then proceeds to block 530. In contrast, if, at block 515, the Scoring Component 250 determines that the selected attribute is not present in the selected patient's EHR data (during the selected time period), the method 500 proceeds to block 520, where the attribute score for the selected attribute is set to zero. The method 500 then proceeds to block 530. In some embodiments, rather than searching for a single occurrence, the Scoring Component 250 determines whether the number of occurrences exceeds a predefined threshold. In one embodiment, the user or administrator defines the number of occurrences that must be satisfied before the attribute is scored a "one." For example, in such an embodiment, the Scoring Component 250 may generate an attribute score of 1 when the number of occurrences exceeds the predefined threshold, indicating that the attribute is present at least the specified number of times. Otherwise, the Scoring Component 250 may set the score to zero to indicate that the attribute is not present at least the specified number of times.

At block 530, the Scoring Component 250 determines whether there are additional attributes to be scored. If so, the method 500 returns to block 510 to select the next attribute. Otherwise, the method 500 proceeds to block 535, where the Scoring Component 250 determines whether there are additional patients for which attribute scores are requested. If so, the method 500 returns to block 505. Otherwise, the method 500 terminates at block 545. Thus, the method 500 can be used to generate binary attribute scores indicating the presence or absence of each individual attribute. These attributes may then be utilized to generate attribute group scores and, ultimately, the concept score for each patient, as discussed below in more detail.

Figure 6:
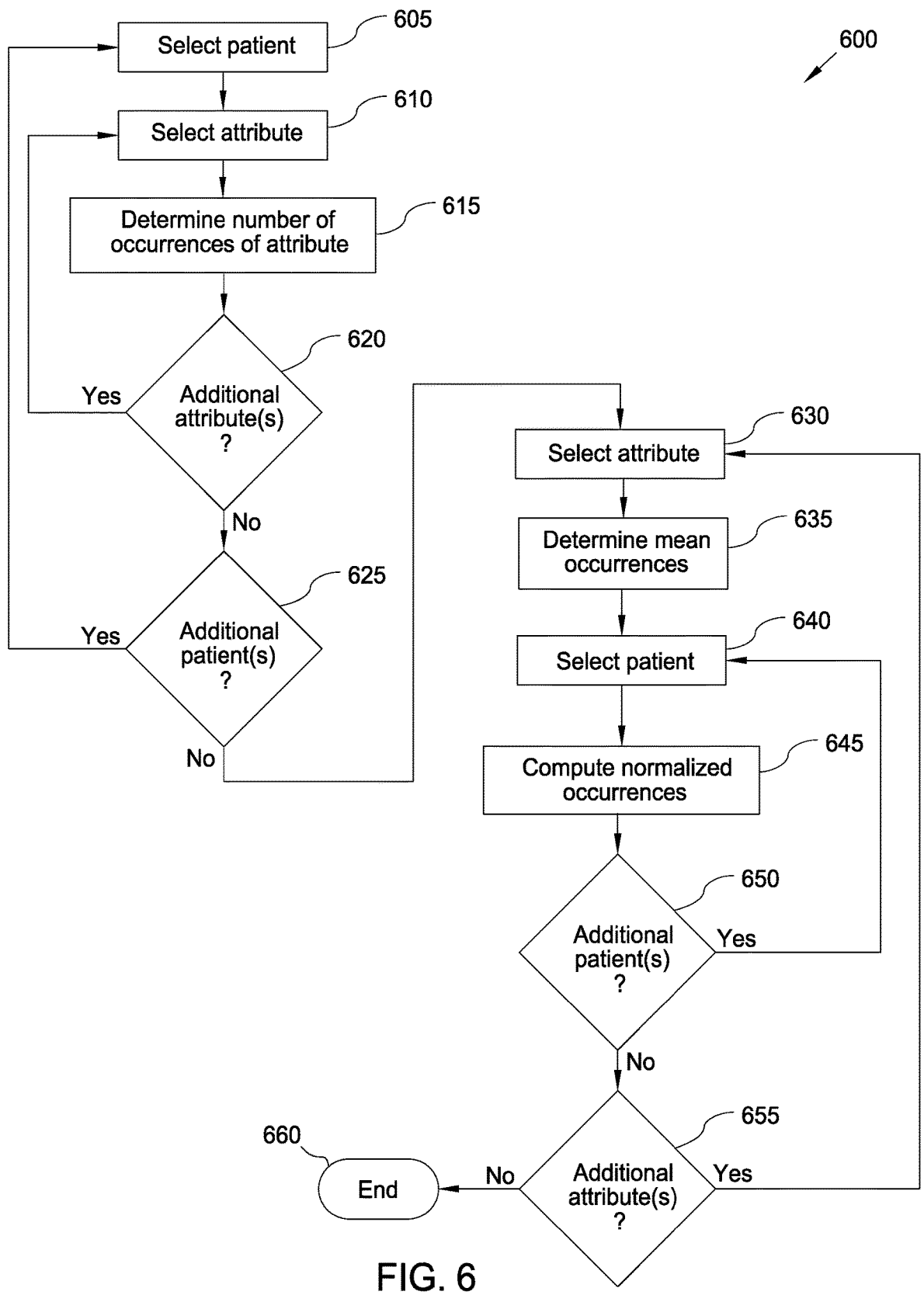
FIG. 6 is a flow diagram illustrating a method for attribute scoring, according to one embodiment disclosed herein.

FIG. 6 is a flow diagram illustrating a method 600 for attribute scoring, according to one embodiment disclosed herein. The method 600 differs from the binary method 500, and corresponds to a linear-scaled scoring algorithm, where each attribute score is based in part on the magnitude of each attribute (e.g., the number of times each attribute is found in the patient's EHR data). The method 600 begins at block 605, where the Scoring Component 250 selects a patient. The method 600 then proceeds to block 610, where the Scoring Component 250 selects an attribute for the identified or selected concept. At block 615, the Scoring Component 250 determines the number of occurrences for the selected attribute in the EHR data of the selected patient. In some embodiments, as discussed above, the Scoring Component 250 may only consider EHR data corresponding to a defined time period. For example, the Scoring Component 250 may determine how many times "depressive disorder" is listed or mentioned in the EHR data of the selected patient during the selected time period. In some embodiments, the attribute score corresponds to this number of occurrences. In the illustrated embodiment, however, this value is normalized, as discussed below.

At block 620, the Scoring Component 250 determines whether there are additional attributes to be processed. If so, the method 600 returns to block 610. Otherwise, the method 600 continues to block 625, where the Scoring Component 250 determines whether there are additional patients in the EHR data that are yet to be processed. In an embodiment, the method 600 generates normalized (e.g., scaled) scores for each attribute based on the data associated with each other patient in the indicated data. Therefore, in one embodiment, the Scoring Component 250 processes data from all patients in the selected cohort before proceeding to generate attribute scores for any particular patient. In some embodiments, the data is normalized within a defined cohort or subset of the patients. In other embodiments, the data is normalized with respect to all patients. Thus, in an embodiment, block 625 comprises determining whether there are additional patients in the subset or plurality of identified patients that are to be considered when generating the normalized attribute scores. If there are additional patients, the method 600 returns to block 605. Otherwise, if occurrence data for each attribute and for each patient has been determined, the method 600 proceeds to block 630.

At block 630, the Scoring Component 250 selects a first attribute for processing. The method continues to block 635, where the Scoring Component 250 determines the mean of the occurrence data for the selected attribute. That is, in the illustrated embodiment, the Scoring Component 250 sums the individual counts for each patient with respect to the selected attribute, in order to determine the mean or average count for the selected attribute across the selected patient population. In some embodiments, the Scoring Component 250 further computes the standard deviation of the data (e.g., the distribution of counts with respect to the selected attribute). In one embodiment, prior to computing the mean and standard deviation, the Scoring Component 250 discards outliers (e.g., patients with a count that exceeds a predefined threshold). In a related embodiment, the Scoring Component 250 computes the mean and standard deviation, and discards patients with a count that exceeds a predefined amount above or below the mean (e.g., more than two standard deviations away from the mean). In one embodiment, the Scoring Component 250 can then normalize the data, with 0.5 corresponding to the mean or average count, 0 corresponding to two standard deviations below the mean, and 1 corresponding to two standard deviations above the mean.

The method 600 then proceeds to block 640, where the Scoring Component 250 selects a patient to generate the attribute score for. In some embodiments, this corresponds to the patient(s) indicated by the user (e.g., the index patient). In some embodiments, the Scoring Component 250 generates attribute scores for each patient, regardless of which patient was selected. At block 645, the Scoring Component 250 computes the normalized attribute score based on the selected patient's occurrence data. For example, as discussed above, in an embodiment, the Scoring Component 250 normalizes the data to between 0 and 1 based on the determined average count, setting two standard deviations above and below the mean to be 1 and 0, respectively. In one embodiment, counts above or below two standard deviations are also assigned a one or zero, respectively. In this way, the selected patient is assigned a score between 0 and 1 indicating the severity or magnitude of the selected attribute during the selected time period.

In some embodiments, the time period utilized to determine the normalized score corresponds to the time period utilized to determine the distribution of scores (e.g., the mean and standard deviation). In some embodiments, however, the distribution may be determined using global data (e.g., corresponding to all time periods) while the final normalized score is based on occurrence data for the particular patient from the selected time period. In such an embodiment, the occurrence data corresponding to all time periods may itself be normalized by dividing the determined count by the number of time periods (e.g., the number of years) that are included in the data. In this way, the Scoring Component 250 can determine the average number of counts during any single year, based on data accumulated over several years. In an embodiment, as discussed above, the patient population to be considered when determining the average and standard deviation can be selected by the healthcare provider, and may correspond to, for example, an identified cohort of the patient, patients with similar conditions, all patients (including healthy patients), and the like. In some embodiments, the Scoring Component 250 can generate multiple attribute scores for a single attribute and a single patient. These scores may correspond to various time periods, or may be normalized based on data from differing populations (e.g., as compared to other schizophrenic patients, and as compared to the total patient population).

At block 650, the Scoring Component 250 then determines whether there are additional patients for which normalized attribute scores should be generated. If so, the method 600 returns to block 640. Otherwise, the method 600 proceeds to block 655, where the Scoring Component 250 determines whether there are additional attributes that have not yet been normalized. If so, the method 600 returns to block 630. Otherwise, the method 600 terminates at block 660. In this way, the Scoring Component 250 can generate normalized linear-scaled scores for each patient with respect to each attribute. These scaled attribute scores allow determination of the severity of the patient's condition, without requiring comparison to other patients. For example, if the attribute score was generated based on a population of patients who were also diagnosed with schizophrenia, the healthcare provider can easily determine whether a patient's attributes are higher or lower than the "average" schizophrenic patient, as well as the magnitude of that difference. Similarly, if the attribute score is generated based on the overall population, the healthcare provider can readily determine whether the patient's attribute scores are higher or lower than the "average" patient. Further, by narrowing the data considered at step 645 to particular time periods, the healthcare provider can determine whether the patient's attributes have changed over time, relative to the selected population. Similarly, the attribute group scores and concept score, which are generated based in part on the attribute scores, can be limited to consideration of specified time periods based on the time period utilized when generating the individual attribute scores.

Figure 7:
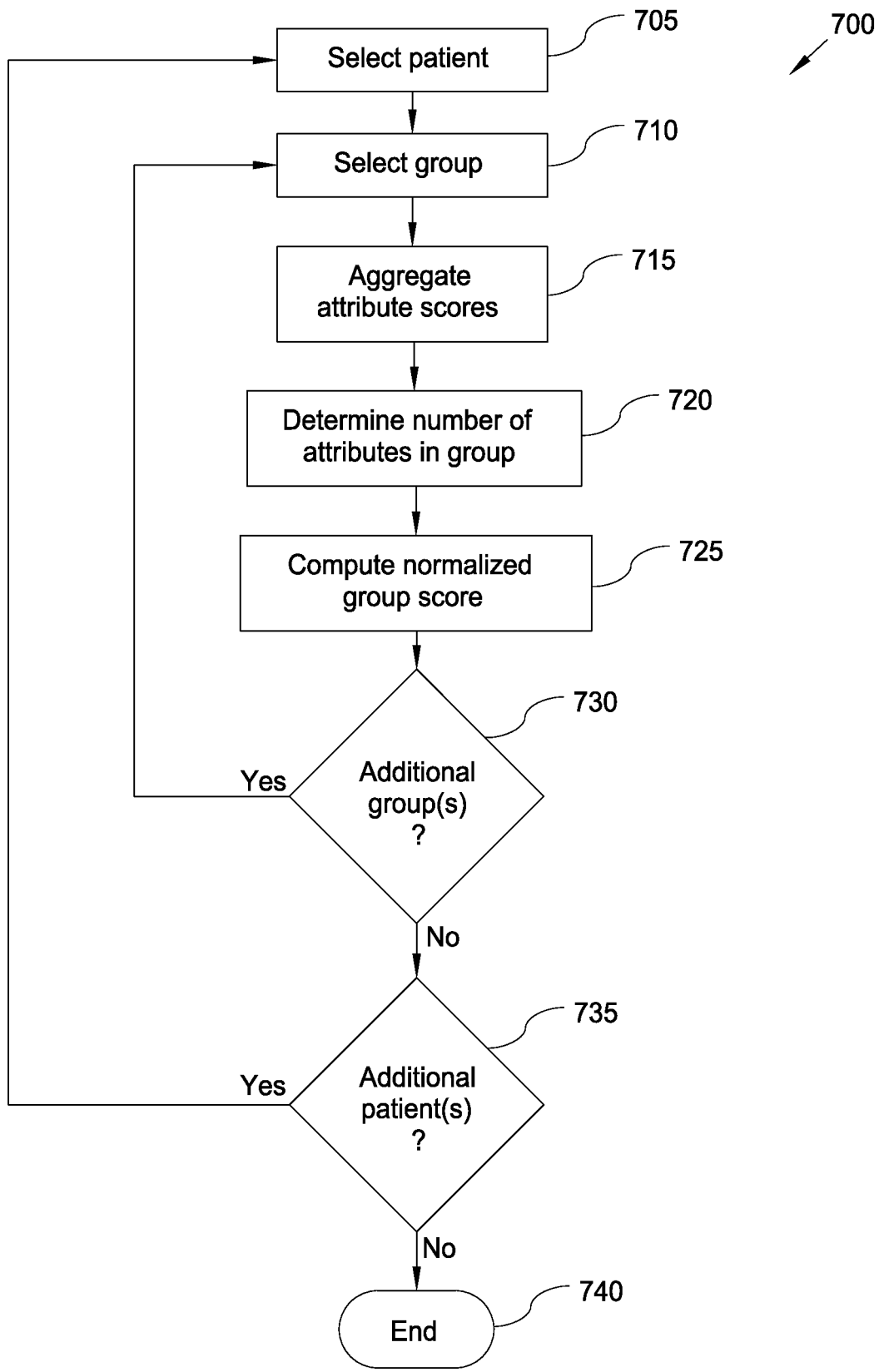
FIG. 7 is a flow diagram illustrating a method for attribute group scoring, according to one embodiment disclosed herein.

FIG. 7 is a flow diagram illustrating a method 700 for attribute group scoring, according to one embodiment disclosed herein. As discussed above, in embodiments, the Attribute Component 240 generates groups of attributes based on factor analysis or primary component analysis. The method 700 may be utilized to generate group scores for each of these attribute groups. The method 700 begins at block 705, where the Scoring Component 250 selects a first patient. As discussed above, in one embodiment, this corresponds to the patient(s) selected by the healthcare provider for analysis. In other embodiments, the Scoring Component 250 generates scores for all patients, regardless of the index patient selected. The method 700 then proceeds to block 710, where the Scoring Component 250 selects an attribute group for the identified concept.

At block 715, the Scoring Component 250 aggregates the attribute scores for each attribute included within the group, with respect to the selected patient. In one embodiment, aggregating the attribute scores comprises performing a linear sum of the scores to generate a total score for the group. In some embodiments, this value is used as the attribute group score for the selected group. In the illustrated embodiment, however, the method 700 proceeds to block 720, where the Scoring Component 250 determines the number of attributes that are included within the group. At block 725, the Scoring Component 250 generates a normalized group score. For example, in an embodiment, the Scoring Component 250 divides the aggregate (e.g., sum) of the attribute scores by the number of attributes in the group, in order to compute a normalized score for the group that takes the size of the group into consideration.

The method 700 then proceeds to block 730, where the Scoring Component 250 determines whether there are additional groups to be scored. If so, the method 700 returns to block 710. Otherwise, the method 700 proceeds to block 735, where the Scoring Component 250 determines whether there are additional patients to be scored. If at least one patient remains, the method 700 returns to block 705. If not, the method 700 terminates at block 740. In some embodiments, rather than utilizing a linear sum, weights are applied to each attribute within the selected group in order to account for the relative importance of each attribute. In one embodiment, this weighting is determined based on user-defined weights. As discussed above, in embodiments, the generated group scores for each attribute group can also be compared across time periods and across patients in order to see how the selected index patient compares to all other patients in the selected population, with respect to each particular attribute group and with respect to the particular concept.

Figure 8:
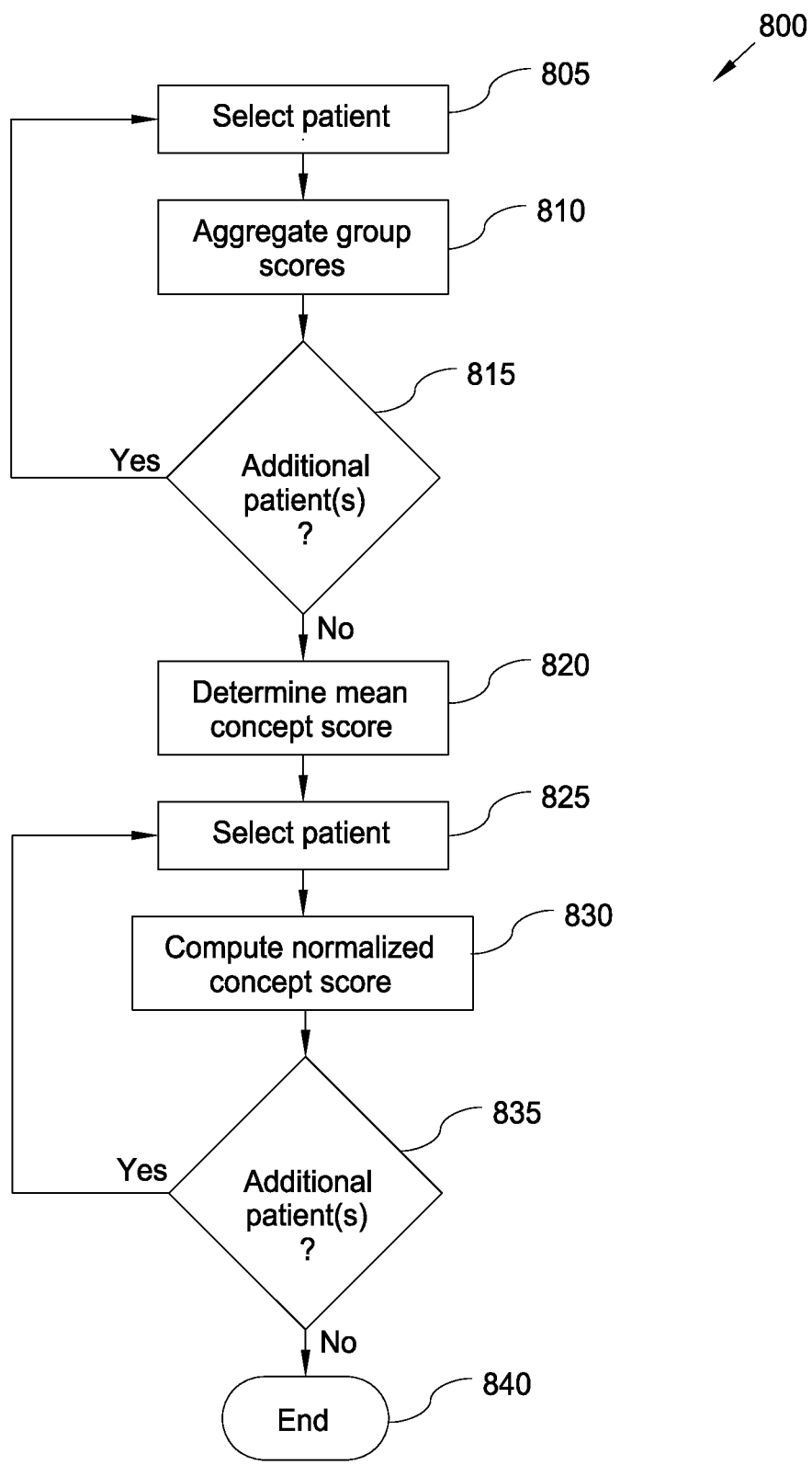
FIG. 8 is a flow diagram illustrating a method for concept scoring, according to one embodiment disclosed herein.

FIG. 8 is a flow diagram illustrating a method 800 for concept scoring, according to one embodiment disclosed herein. The method 800 begins at block 805, where the Scoring Component 250 selects a patient. At block 810, the Scoring Component 250 aggregates the individual attribute group scores of the selected patient. For example, in one embodiment, the Scoring Component 250 computes the sum of the group scores. In some embodiments, the Scoring Component 250 determines the mean or median of the attribute group scores for the particular patient. In some embodiments, this aggregate score is used as the concept score for the selected patient, and no further processing is required. In the illustrated embodiment, however, the aggregate score is normalized to generate the final concept score for each patient.

As illustrated, the method 800 continues to block 815, where the Scoring Component 250 determines whether there are additional patients to be considered. As discussed above, in some embodiments, the concept score for a particular patient is normalized based on a selected subset of patients, which may correspond to a cohort of the index patient, other patients with similar conditions, all patients regardless of condition, and the like. If there are additional patients that are to be considered, the method 800 returns to block 805. If not, the method 800 proceeds to block 820, where the Scoring Component 250 determines the mean concept score for all of the patients under consideration, based on the aggregated group scores (i.e., the individual concept scores) for each patient. In some embodiments, in addition to determining the mean concept score, the Scoring Component 250 computes the standard deviation of the concept scores as well.

At block 825, the Scoring Component 250 selects a patient to generate a final normalized concept score for. In one embodiment, this corresponds to the index patient indicated by the user. In other embodiments, the Scoring Component 250 may generate a normalized score for multiple patients. At block 830, the Scoring Component 250 generates a normalized concept score for the selected patient. In some embodiments, the Scoring Component 250 may normalize the aggregated attribute group scores for the selected patient to a predefined range (such as between zero and one) based on the determined mean and standard deviation for the selected cohort of patients. For example, in one embodiment, a normalized concept score of "1" or "0" is assigned to patients with aggregate group scores that exceed two standard deviations above or below the mean, respectively. In such an embodiment, patients are similarly distributed on the number scale between zero and one based on their scores. At block 835, the Scoring Component 250 determines whether there are additional patients for which to generate a normalized concept score. If so, the method 800 returns to block 825. If no patients remain, the method 800 terminates at block 840.

In some embodiments, the concept score for each patient is determined based on linear aggregation that gives equal weights to each of the attribute group scores. In other embodiments, various weighting can be utilized to account for more important and less important attribute groups. For example, in one embodiment, when aggregating the group scores, each attribute group score is assigned a weight based at least in part on the number of attributes within the group, or based on a user-defined importance. In some embodiments, the importance of each attribute group may similarly be determined based on analyzing literature, such as with one or more cognitive tools. In one embodiment, the weighting of each attribute group score is based at least in part on how each respective group score compares to other patients in the selected cohort. For example, in one embodiment, group scores that are further from the mean group score for the respective group are afforded higher weight when generating the concept score for the respective patient.

Similarly, in some embodiments, each attribute group score for a patient is determined based on linear aggregation of each attribute score. In other embodiments, the individual attribute scores may similarly be weighted when generating the group score for the respective group of attributes. For example, in one embodiment, the user may assign differing weights to each attribute, or a weight may be determined based on a cognitive analysis of the medical literature identifying attributes which are more important. This may be based on, for example, determining attributes which appear frequently in the literature, or which are often treated as relatively important.

Embodiments of the present disclosure enable cognitive generation of concept scores for any number of clinical concepts. In an embodiment, a user (e.g., a healthcare provider) may select the concept or theme he or she is interested in analyzing, and provide this concept to the Concept Scoring Application 230 (e.g., in a natural language format). Similarly, the user may provide an indication as to the index patient that is being analyzed, as well as one or more cohorts of patients to which the index patient should be compared and one or more time periods that should be considered. Of course, in embodiments, the embodiments described herein can be utilized to process any concept.

In some embodiments, a concept score may be automatically generated for a number of predefined concepts for each patient, prior to the user selecting any particular patient. For example, in one embodiment, one or more concept scores may be pre-computed based on a configuration selected by the user or an administrator. In one embodiment, for each respective patient, one or more concepts are selected concepts based on determining that the selected concepts are particularly important or are often relied upon for patients that are similar to the respective patient. For example, one or more predefined concepts may be identified as likely to be relevant, based on analysis of the patient's EHRs (e.g., based on a diagnosis or other attribute of the patient). In this way, when a healthcare provider accesses the patient's data, the relevant concepts or themes may have already been scored.

Figure 9:
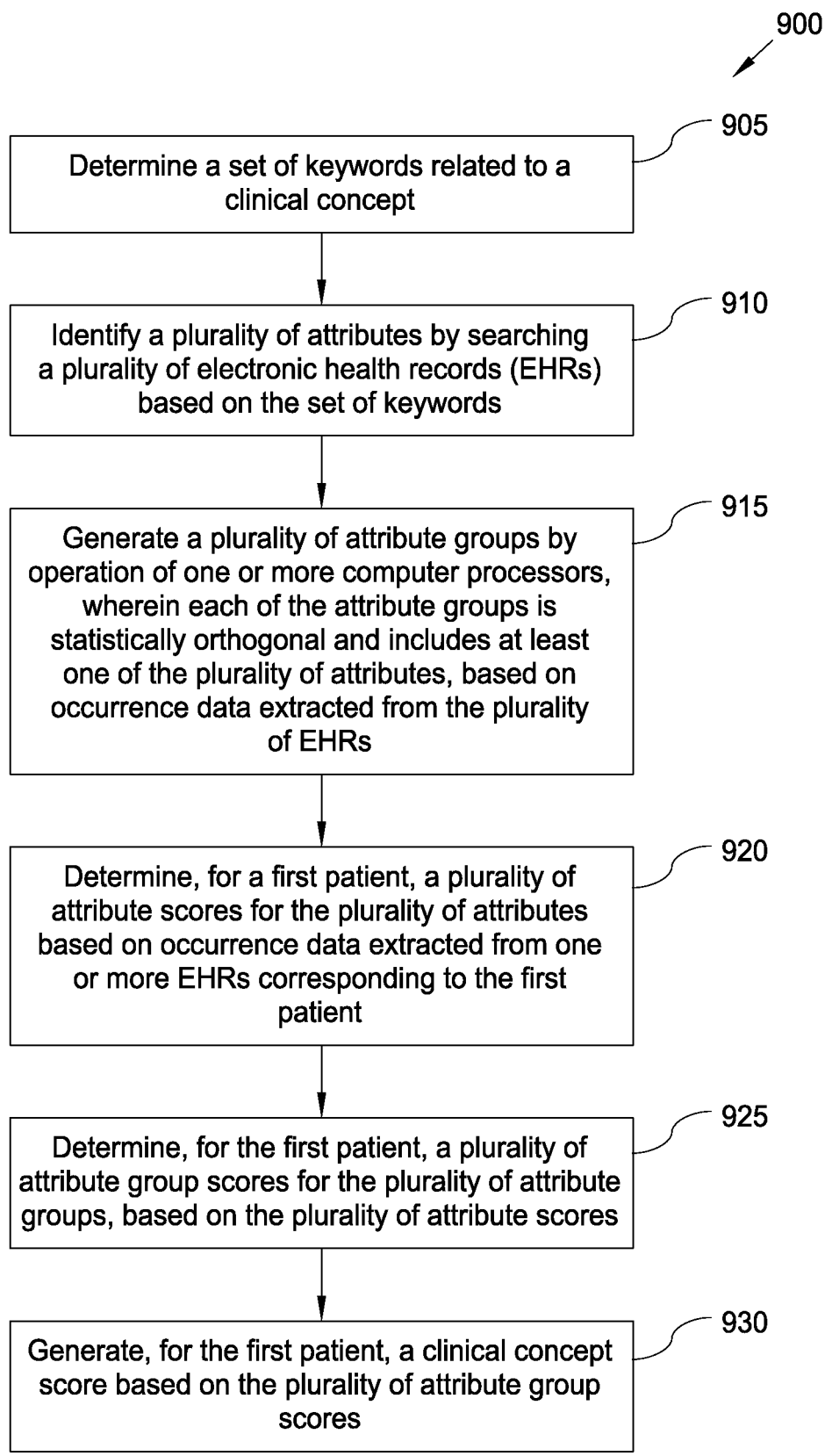
FIG. 9 is a flow diagram illustrating a method for generating clinical concept scores, according to one embodiment disclosed herein.

FIG. 9 is a flow diagram illustrating a method 900 for generating clinical concept scores, according to one embodiment disclosed herein. The method 900 begins at block 905, where the Concept Scoring Application 230 determines a set of keywords related to a clinical concept. At block 910, the Concept Scoring Application 230 identifies a plurality of attributes by searching a plurality of EHRs based on the set of keywords. The method 900 then continues to block 915, where the Concept Scoring Application 230 generates a plurality of attribute groups by operation of one or more computer processors, wherein each of the attribute groups is statistically orthogonal and includes at least one of the plurality of attributes, based on occurrence data extracted from the plurality of EHRs. At block 920, the Concept Scoring Application 230 determines, for a first patient, a plurality of attribute scores for the plurality of attributes based on occurrence data extracted from one or more EHRs corresponding to the first patient. Further, the method 900 proceeds to block 925, where the Concept Scoring Application 230 determines, for the first patient, a plurality of attribute group scores for the plurality of attribute groups, based on the plurality of attribute scores. Finally, at block 930, the Concept Scoring Application 230 generates, for the first patient, a clinical concept score based on the plurality of attribute group scores.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Concept Scoring Application 230) or related data available in the cloud. For example, the Concept Scoring Application 230 could execute on a computing system in the cloud and generate concept scores for any number of patients and concepts. In such a case, the Concept Scoring Application 230 could analyze electronic health records and store concept scores, attribute group scores, and attribute scores at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for scoring clinical concepts, the method comprising:
 generating a set of keywords related to a clinical concept using one or more machine learning models, comprising parsing medical literature based on the clinical concept to identify related concepts and keywords;
 identifying a plurality of attributes by searching a plurality of electronic health records (EHRs) based on the set of keywords;
 generating a plurality of attribute groups based on occurrence data extracted from the plurality of EHRs, wherein the plurality of attribute groups are generated by performing factor analysis by operation of one or more computer processors, such that the attribute groups are statistically orthogonal and each has an independent effect on the clinical concept, and wherein each of the plurality of attribute groups includes at least one of the plurality of attributes;
 storing the set of keywords, plurality of attributes, and plurality of attribute groups, in association with the clinical concept, for future use;
 determining, for a first patient, a plurality of attribute scores for the plurality of attributes based on occurrence data extracted from one or more EHRs corresponding to the first patient, comprising:
  determining a first occurrence count for a first attribute of the plurality of attributes with respect to the first patient;
  determining a standard deviation of occurrence counts with respect to a cohort of patients; and
  generating a first attribute score for the first attribute for the first patient by normalizing the first occurrence count based on the standard deviation of occurrence counts;
 determining, for the first patient, a plurality of attribute group scores for the plurality of attribute groups, based on the plurality of attribute scores;
 generating, for the first patient, a first clinical concept score based on the plurality of attribute group scores, wherein the first clinical concept score is an objective measure of how severe the clinical concept is, with respect to the first patient;
 facilitating improved medical care for the first patient, based on the first clinical concept score;
 receiving a request to generate, for a second patient, a second clinical concept score with respect to the clinical concept; and
 in response to determining that the set of keywords, plurality of attributes, and plurality of attribute groups were stored in association with the clinical concept:
  refraining from regenerating keywords for the clinical concept;
  refraining from reselecting attributes for the clinical concept;
  refraining from reprocessing attributes to define attribute groups; and
  generating the second clinical concept score based on the stored set of keywords, plurality of attributes, and plurality of attribute groups.

2. The method of claim 1, wherein determining the plurality of attribute scores for the first patient comprises, for each respective attribute of the plurality of attributes, analyzing EHRs associated with the first patient to determine whether the respective attribute is present.

3. The method of claim 1, wherein determining the plurality of attribute scores for the first patient comprises, for each respective attribute of the plurality of attributes:
 analyzing EHRs associated with each respective patient of a plurality of patients to determine respective occurrence data of the respective attribute; and
 determining, for each of the plurality of patients, an attribute score for the respective attribute by normalizing the respective occurrence data.

4. The method of claim 1, wherein determining the plurality of attribute group scores for the first patient comprises, for each respective attribute group in the plurality of attribute groups, aggregating one or more attribute scores in the plurality of attribute scores, wherein the one or more attribute scores correspond to one or more attributes that are included within the respective attribute group.

5. The method of claim 4, wherein generating the first clinical concept score for the first patient comprises aggregating the plurality of attribute group scores.

6. The method of claim 5, the method further comprising generating a respective clinical concept score for each respective patient in a plurality of patients.

7. The method of claim 1, wherein determining the set of keywords comprises using one or more cognitive tools to generate the set of keywords based on the clinical concept.

8. The method of claim 1, wherein, prior to identifying the plurality of attributes, the set of keywords are optionally clinically validated by a subject matter expert.

9. The method of claim 1, wherein at least one of the plurality of attributes corresponds to one of:
   (i) a diagnosis;
   (ii) a finding;
   (iii) a lab result;
   (iv) an observation;
   (v) a procedure;
   (vi) a drug;
   (vii) a gene;
   (viii) a single nucleotide polymorphism (SNP); or
   (ix) an encounter.

10. A computer program product comprising a computer-readable storage medium having computer-readable program code embodied therewith, the computer-readable program code executable by one or more computer processors to perform an operation comprising:
   generating a set of keywords related to a clinical concept using one or more machine learning models, comprising parsing medical literature based on the clinical concept to identify related concepts and keywords;
   identifying a plurality of attributes by searching a plurality of electronic health records (EHRs) based on the set of keywords;
   generating a plurality of attribute groups based on occurrence data extracted from the plurality of EHRs, wherein the plurality of attribute groups are generated by performing factor analysis by operation of one or more computer processors, such that the attribute groups are statistically orthogonal and each has an independent effect on the clinical concept, and wherein each of the plurality of attribute groups includes at least one of the plurality of attributes;
   storing the set of keywords, plurality of attributes, and plurality of attribute groups, in association with the clinical concept, for future use;
   determining, for a first patient, a plurality of attribute scores for the plurality of attributes based on occurrence data extracted from one or more EHRs corresponding to the first patient, comprising:
      determining a first occurrence count for a first attribute of the plurality of attributes with respect to the first patient;
      determining a standard deviation of occurrence counts with respect to a cohort of patients; and
      generating a first attribute score for the first attribute for the first patient by normalizing the first occurrence count based on the standard deviation of occurrence counts;
   determining, for the first patient, a plurality of attribute group scores for the plurality of attribute groups, based on the plurality of attribute scores;
   generating, for the first patient, a first clinical concept score based on the plurality of attribute group scores, wherein the first clinical concept score is an objective measure of how severe the clinical concept is, with respect to the first patient;
   facilitating improved medical care for the first patient, based on the first clinical concept score;
   receiving a request to generate, for a second patient, a second clinical concept score with respect to the clinical concept; and
   in response to determining that the set of keywords, plurality of attributes, and plurality of attribute groups were stored in association with the clinical concept:
      refraining from regenerating keywords for the clinical concept;
      refraining from reselecting attributes for the clinical concept;
      refraining from reprocessing attributes to define attribute croups; and
      generating the second clinical concept score based on the stored set of keywords, plurality of attributes, and plurality of attribute groups.

11. The computer program product of claim 10, wherein determining the plurality of attribute scores for the first patient comprises, for each respective attribute of the plurality of attributes, analyzing EHRs associated with the first patient to determine whether the respective attribute is present.

12. The computer program product of claim 10, wherein determining the plurality of attribute scores for the first patient comprises, for each respective attribute of the plurality of attributes:
   analyzing EHRs associated with each respective patient of a plurality of patients to determine respective occurrence data of the respective attribute; and
   determining, for each of the plurality of patients, an attribute score for the respective attribute by normalizing the respective occurrence data.

13. The computer program product of claim 10, wherein determining the plurality of attribute group scores for the first patient comprises, for each respective attribute group in the plurality of attribute groups, aggregating one or more attribute scores in the plurality of attribute scores, wherein the one or more attribute scores correspond to one or more attributes that are included within the respective attribute group.

14. The computer program product of claim 13, wherein generating the clinical concept score for the first patient comprises aggregating the plurality of attribute group scores.

15. The computer program product of claim 10, wherein determining the set of keywords comprises using one or more cognitive tools to generate the set of keywords based on the clinical concept.

16. A system comprising:
   one or more computer processors; and
   a memory containing a program which when executed by the one or more computer processors performs an operation, the operation comprising:
      generating a set of keywords related to a clinical concept using one or more machine learning models, comprising parsing medical literature based on the clinical concept to identify related concepts and keywords;
      identifying a plurality of attributes by searching a plurality of electronic health records (EHRs) based on the set of keywords;
      generating a plurality of attribute groups based on occurrence data extracted from the plurality of EHRs, wherein the plurality of attribute groups are generated by performing factor analysis by operation of one or more computer processors, such that the attribute groups are statistically orthogonal and each has an independent effect on the clinical concept, and wherein each of the plurality of attribute groups includes at least one of the plurality of attributes;

storing the set of keywords, plurality of attributes, and plurality of attribute groups, in association with the clinical concept, for future use;

determining, for a first patient, a plurality of attribute scores for the plurality of attributes based on occurrence data extracted from one or more EHRs corresponding to the first patient, comprising:
  determining a first occurrence count for a first attribute of the plurality of attributes with respect to the first patient;
  determining a standard deviation of occurrence counts with respect to a cohort of patients; and
  generating a first attribute score for the first attribute for the first patient by normalizing the first occurrence count based on the standard deviation of occurrence counts;

determining, for the first patient, a plurality of attribute group scores for the plurality of attribute groups, based on the plurality of attribute scores;

generating, for the first patient, a first clinical concept score based on the plurality of attribute group scores, wherein the first clinical concept score is an objective measure of how severe the clinical concept is, with respect to the first patient;

facilitating improved medical care for the first patient, based on the first clinical concept score;

receiving a request to generate, for a second patient, a second clinical concept score with respect to the clinical concept; and in response to determining that the set of keywords, plurality of attributes, and plurality of attribute groups were stored in association with the clinical concept:
  refraining from regenerating keywords for the clinical concept;
  refraining from reselecting attributes for the clinical concept;
  refraining from reprocessing attributes to define attribute groups; and
  generating the second clinical concept score based on the stored set of keywords, plurality of attributes, and plurality of attribute groups.

17. The system of claim 16, wherein determining the plurality of attribute scores for the first patient comprises, for each respective attribute of the plurality of attributes, analyzing EHRs associated with the first patient to determine whether the respective attribute is present.

18. The system of claim 16, wherein determining the plurality of attribute scores for the first patient comprises, for each respective attribute of the plurality of attributes:
  analyzing EHRs associated with each respective patient of a plurality of patients to determine respective occurrence data of the respective attribute; and
  determining, for each of the plurality of patients, an attribute score for the respective attribute by normalizing the respective occurrence data.

19. The system of claim 16, wherein determining the plurality of attribute group scores for the first patient comprises, for each respective attribute group in the plurality of attribute groups, aggregating one or more attribute scores in the plurality of attribute scores, wherein the one or more attribute scores correspond to one or more attributes that are included within the respective attribute group.

20. The system of claim 19, wherein generating the clinical concept score for the first patient comprises aggregating the plurality of attribute group scores.

* * * * *